United States Patent [19]

Yamada

[11] Patent Number: 5,314,640
[45] Date of Patent: May 24, 1994

[54] TOLAN DERIVATIVES, LIQUID CRYSTAL COMPOSITIONS INCLUDING SAME, LIQUID CRYSTAL DISPLAY DEVICES INCLUDING THE COMPOSITIONS AND METHOD OF PREPARATION

[75] Inventor: Shuhei Yamada, Suwa, Japan

[73] Assignee: Seiko Epson Corporation, Nagano, Japan

[21] Appl. No.: 652,818

[22] Filed: Feb. 8, 1991

[30] Foreign Application Priority Data

| Feb. 16, 1990 | [JP] | Japan | 2-35692 |
| Feb. 23, 1990 | [JP] | Japan | 2-55570 |
| Apr. 12, 1990 | [JP] | Japan | 2-96916 |
| Jun. 5, 1990 | [JP] | Japan | 2-146766 |
| Jun. 6, 1990 | [JP] | Japan | 2-148095 |

[51] Int. Cl.$^5$ ............... C09K 19/06; C09K 19/30; C09K 19/12; C07C 255/00
[52] U.S. Cl. ............... 252/299.6; 252/299.63; 252/299.66; 252/299.01
[58] Field of Search ............... 252/299.6, 299.5, 299.63, 252/299.01; 350/350 R; 570/128, 144; 585/23; 558/416

[56] References Cited

U.S. PATENT DOCUMENTS

| 4,003,844 | 1/1977 | Sorkin | 252/299.66 X |
| 4,705,870 | 11/1987 | Takatsu et al. | 549/369 |
| 4,705,905 | 11/1987 | Takatsu et al. | 585/25 |
| 4,713,468 | 12/1987 | Takatsu et al. | 558/411 |
| 4,726,910 | 2/1988 | Takatsu et al. | 252/299.5 |
| 4,726,911 | 2/1988 | Krause et al. | 252/299.61 |
| 4,797,228 | 1/1989 | Goto et al. | 252/299.63 |
| 4,820,878 | 4/1989 | Takatsu et al. | 568/659 |
| 4,839,091 | 6/1989 | Goto et al. | 252/299.63 |
| 4,853,152 | 8/1989 | Goto | 252/299.63 |
| 4,883,609 | 11/1989 | Yamada | 252/299.61 |
| 4,908,152 | 3/1990 | Goto | 252/299.63 |
| 5,068,053 | 11/1991 | Reiffenrath et al. | 252/299.61 |

FOREIGN PATENT DOCUMENTS

| 377516 | 7/1990 | European Pat. Off. |
| 2504641 | 8/1976 | Fed. Rep. of Germany |
| 3906038 | 9/1989 | Fed. Rep. of Germany |
| 155142 | 8/1985 | Japan |

OTHER PUBLICATIONS

Gray, et al., "Mesomorphic Transition Temperatures..", *Mol. Cryst. Liq. Crst.*, 1976, vol. 37, pp. 213-231.
Fieser et al. *Organic Chemistry* 3rd edition (1956) pp. 86-87.

Primary Examiner—Robert L. Stoll
Assistant Examiner—C. Harris
Attorney, Agent, or Firm—Blum Kaplan

[57] ABSTRACT

A tolan derivative suitable for use in a liquid crystal composition represented by the general formula:

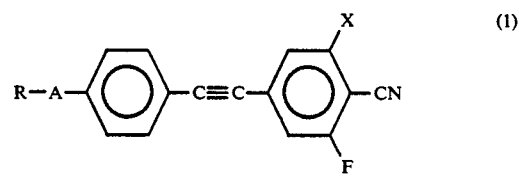

wherein R is a straight chain alkyl group having from 1 to 10 carbon atoms, A is either

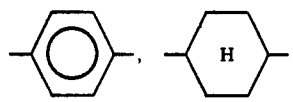

or a single bond, and X is hydrogen or fluorine.

26 Claims, 1 Drawing Sheet

U.S. Patent  May 24, 1994  5,314,640
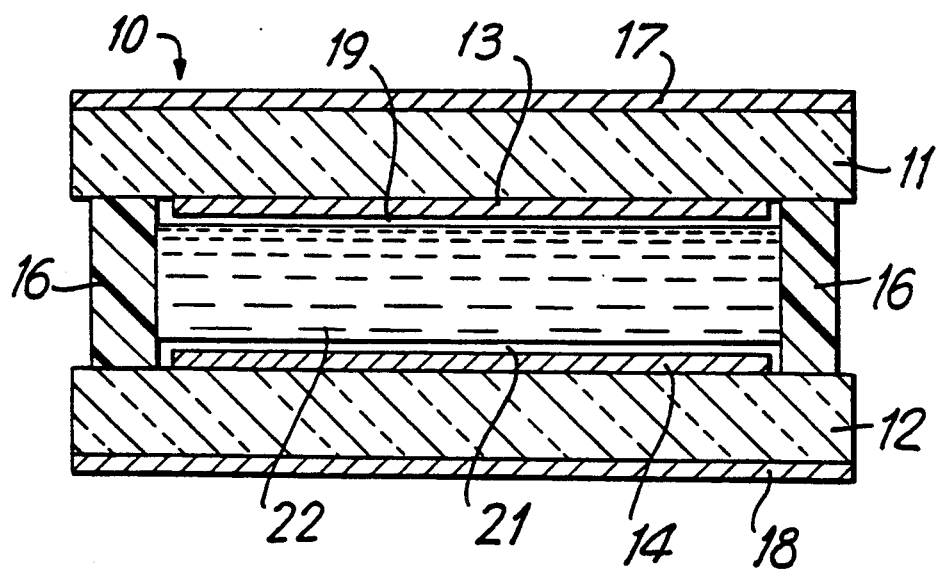

TOLAN DERIVATIVES, LIQUID CRYSTAL COMPOSITIONS INCLUDING SAME, LIQUID CRYSTAL DISPLAY DEVICES INCLUDING THE COMPOSITIONS AND METHOD OF PREPARATION

BACKGROUND OF THE INVENTION

This invention relates to liquid crystal compounds and, more particularly, novel tolan derivatives, liquid crystal compositions containing the tolan derivatives and liquid crystal display devices including the compositions.

Liquid crystal display devices utilize the electro-optical properties of liquid crystal materials. Liquid crystal materials have three phases which are known as the nematic phase, the cholesteric phase and the smectic phase. The display system most widely used at present is the twisted nematic type ("TN") which uses the nematic phase of liquid crystal materials.

The advantages of liquid crystal display devices is that they can be compact and thin. Additionally, liquid crystal display devices are driven by low voltage and so require only a small amount of electric power. Liquid crystal display devices are also light-receiving elements and so cause limited eye fatigue to the user even after extended viewing. Because of these advantages, liquid crystal display devices have been used widely in watches, desk-top calculators, audio devices, measuring instruments, automobile dashboards and the like. More recently, liquid crystal materials have been used in displays containing numerous picture elements such as black-and-white or color pocket televisions. Similarly, liquid crystal display devices have begun to replace CRTs in personal computers and word processors.

Although the required characteristics for liquid crystal material varies depending upon in which type of device the material is to be used, all liquid crystal materials must have the following characteristics:

1. the material must be transparent as well as electrically and chemically stable even when exposed to heat and light;
2. the material must perform in a wide range of temperatures;
3. the electro-optical response speed of the material must be rapid;
4. the voltage required to drive the material must be low;
5. the material must need only a small incremental change in voltage to cause a sharp change in the material between the activated and non-activated states, and the temperature dependence of the threshold voltage value ("$V_{th}$") must be small; and
6. the material must provide a wide visual angle range at which the device may be viewed.

A number of known liquid crystals satisfy the first characteristic. However, no single liquid crystal compound is known which, by itself, satisfies the second through sixth characteristics. Thus, in order to have all six characteristics, a liquid crystal composition must contain several kinds of nematic liquid crystal compounds or non-liquid crystal compounds, each compound possessing one or more of the desired characteristics.

To satisfy the second characteristic, at least two liquid crystal compounds are used. The first compound has a relatively low molecular weight and has a crystal-nematic transition point (the "C-N" point) or melting point at or about room temperature. The second compound has a relatively high molecular weight with a transition temperature between phases (the "N-I" point) of 200° C. or more. The N-I point of the second compound is ideally as high as possible to provide the maximum temperature range at which the liquid crystal composition may perform.

In order to satisfy the third characteristic, it is necessary to decrease the cell gap (designated "d") in the liquid crystal compound to increase the response speed (designated "r") because of the following relationship:

$$r \alpha \eta / d$$

whereby $\eta$ is the viscosity index. However, to prevent generation of interference fringes on the surface of cells which deteriorate the appearance of cells, the value $\Delta n \cdot d$ should be a constant value. Therefore, the liquid crystal compound should have a large $\Delta n$ so that the value of d can be small to increase the response speed.

To satisfy the fourth characteristic, the liquid crystal compound should require a low threshold voltage. The following is the relation between $V_{th}$, the elastic constant K and $\Delta \epsilon$:

$$V_{th} \alpha (K/\Delta \epsilon)^{\frac{1}{2}}$$

Thus, in order to decrease $V_{th}$, the liquid crystal compound should have a large $\Delta \epsilon$ and a small K.

Accordingly, it is desirable to provide a liquid crystal compound to be used in a liquid crystal composition which not only has the first characteristic listed above, but which also satisfies the upper temperature limit of the second characteristic as well as having the third and fourth characteristics.

SUMMARY OF THE INVENTION

Generally speaking, in accordance with the invention, a tolan derivative represented by the general formula:

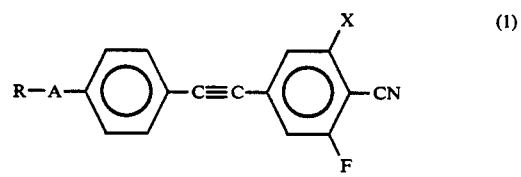

wherein R is a straight chain alkyl group having from 1 to 10 carbon atoms, A is either

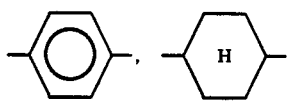

or a single bond, and X is hydrogen or fluorine, which can be included in a liquid crystal compound to improve performance of a liquid crystal display device, is provided. Generally, the tolan derivative is included in an amount between about 2 to 20 weight percent based on a total weight of the composition.

Accordingly, it is an object of this invention to provide a novel liquid crystal compound.

Another object of the invention is to provide a liquid crystal compound which is transparent as well as electrically and chemically stable even when exposed to heat and light.

Still another object of the invention is to provide a liquid crystal compound which performs well at high temperatures.

A further object of the invention is to provide a liquid crystal compound which has a relatively high molecular weight and a high crystal-nematic transition point.

Yet another object of the invention is to provide a liquid crystal compound which has a rapid electro-optical response.

Still another object of the invention is to provide a liquid crystal compound which has a large Δn.

A further object of the invention is to provide a liquid crystal compound which requires a low driving voltage.

Still another object of the invention is to provide a liquid crystal compound which has a large Δε and a small K.

Yet another object of the invention is to provide a liquid crystal compound which simultaneously fulfills all the above given objects of the invention.

Still other objects and advantages of the invention will in part be obvious and will in part be apparent from the specification.

The invention accordingly comprises a composition of matter possessing the characteristics, properties, and the relation of constituents, the several steps and the relation of one or more of such steps with respect to each of the others, and the apparatus embodying features of construction, combination and arrangement of parts which are adapted to effect such steps, all as exemplified in the detailed disclosure hereinafter set forth, and the scope of the invention will be indicated in the claims.

BRIEF DESCRIPTION OF THE DRAWING

For a fuller understanding of the invention, reference is had to the following description taken in connection with the accompanying drawing, in which:

FIG. 1 is a sectional view of a liquid crystal element in accordance with the invention.

DESCRIPTION OF THE PREFERRED EMBODIMENTS

A liquid crystal display device 10 constructed in accordance with the invention is shown in cross-section in FIG. 1. Display device 10 includes an upper and lower spaced apart glass substrates 11 and 12, respectively. An electrode pattern 13 is selectively disposed on the interior surface of substrate 11 and a cooperating electrode pattern 14 is disposed on the interior surface of lower substrate 12. A sealing member 16 about the periphery of the display seals the space between the substrates. An upper polarizing plate 17 is disposed on the outer surface of upper substrate 11 and a lower polarizing plate 18 is disposed on the outer surface of lower substrate 12. An orientation-regulating layer 19 and 21 is deposited across each electrode pattern 13 and 14 respectively. A liquid crystal composition 22 is disposed in the space between substrates 11 and 12.

Liquid crystal composition 22 includes the tolan-derivative liquid crystal compound having the general formula (1) as follows:

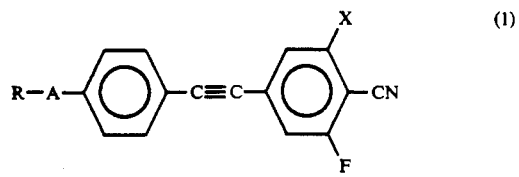

wherein R is a straight chain alkyl group having from 1 to 10 carbon atoms, A is either

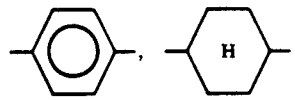

or a single bond, and X is hydrogen or fluorine. The tolan derivatives of formula (1) can be prepared in accordance with the invention by the step shown by way of example in the following Reaction Scheme.

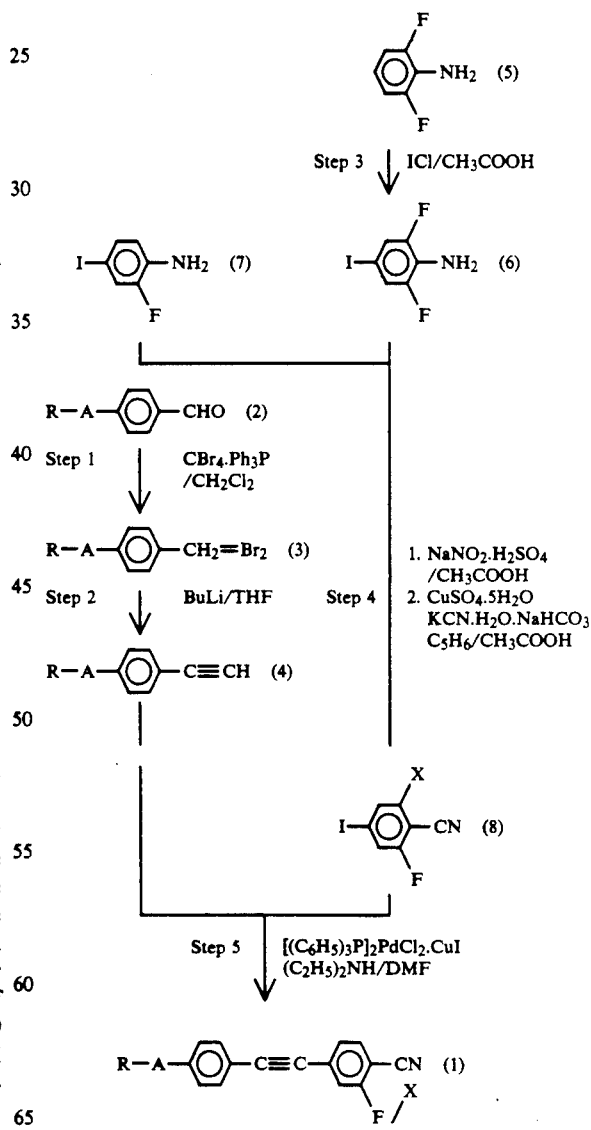

Step 1: A 4-alkylbenzaldehyde compound (2) is reacted with carbon tetrabromide and triphenylphosphine in dichloromethane to yield a 4 alkyl-β,β-dibromostyrene compound (3).

Step 2: The 4 alkyl-β,β-dibromostyrene compound (3) is reacted with butyl lithium in tetrahydrofuran to yield a 4-alkylphenylacetylene compound (4).

Step 3: 2,6-difluoroaniline (5) is reacted with iodine chloride in acetic acid to yield 2,6-difluoro-4-iodaniline (6).

Step 4: Either 2,6-difluoro-4-iodaniline (6) or 2-6-difluoro-4-iodoaniline (7) if Step 3 is omitted is reacted with sodium nitrite and sulfuric acid in acetic acid to form a diazonium salt, followed by reaction with sulfuric acid and potassium cyanide to yield a 1-cyano-2-fluoro-4-iodobenzene or 1-cyano-2,6-difluoro iodobenzene (8).

Step 5: The 4-alkylphenylacetylene (4) is reacted with the iodobenzene compound (8) in N,N-dimethylformamide in the presence of bis(triphenylphosphine) palladium (II) chloride, cuprous iodide, and diethylamine to obtain the tolan-derivative liquid crystal compound of formula (1).

The following examples are set forth by way of illustration to show preparation of the tolan derivatives in accordance with the invention. They are set forth for purposes of illustration only, and are not intended in a limiting sense.

Example 1 (Synthesis of Compound 1-a)

Production of 4-propyl-3'-fluoro-4'-cyanotolan.

Step 1: 60 g of carbon tetrabromide was dissolved in 180 ml of dichloromethane, and 93 g of triphenylphosphine was added at 0° C. or less. Next, 22 g of 4-propylbanzaldehyde was dissolved in 150 ml of dichloromethane, which then was added dropwise to the first dichloromethane solution over a period of one hour. The combined solutions were then agitated at room temperature for one hour. After completion of the reaction, the dichloromethane was distilled off, and 500 ml hexane was added to the residue. The resulting crystals were filtrated and further washed with hexane three times. The residue was subjected to vacuum distillation (120 to 130° C./4 mmHg) to obtain 27 g of 4-propyl-β,β-dibromostyrene.

Step 2: Under nitrogen flow, the 27 g of 4-propyl-β,β-dibromostyrene was dissolved in 44 ml of tetrahydrofuran and cooled to −78° C. Two hundred ml of a butyl lithium hexane solution (1.6 mol/l was added dropwise therein over a period of one hour. The solution was then agitated at room temperature for one and a half hours. After completion of the reaction, 200 ml of water was added. The crystals then were extracted with chloroform and washed three times with water. The remaining chloroform was distilled off, after which vacuum distillation (70° to 75° C./20 mmHg) was carried out to obtain 3.5 g of 4-propylphenylacetylene.

Step 3: Omitted.

Step 4: 27 g of sodium nitrite was dissolved in 205 ml of sulfuric acid and cooled to 10° C. or less, and then 238 ml of acetic acid was added. At 20° to 25° C., 65 g of 2-fluoro-4-iodoaniline was added to the solution, and then the solution was agitated for one hour. A second solution was made by dissolving 83 g of copper sulfate pentahydrate in 20.5 ml of water, to which was added 140 g of ice, and this solution was added to the first. A third solution containing 88 g of potassium cyanide dissolved in 200 ml of water, 500 g of sodium bicarbonate, and 200 ml of benzene was added to the first solution, and a diazonium salt sulfuric acid solution was added therein. After agitation at room temperature for 3 hours, a sodium hydroxide aqueous solution was added to dissolve the crystals. After being extracted with chloroform, the crystals were washed three times alternating with a 10% sodium hydroxide solution and water. After distillation of the chloroform, the residue was extracted with hexane, and the hexane was distilled off. This residue was subjected to vacuum distillation (95° to 110° C./15 mmHg), and further recrystallized to obtain 20 g of 1-cyano-2-fluoro-4-iodobenzene.

Step 5: 2.1 g of this 1-cyano-2-fluoro-4-iodobenzene was dissolved in 14 ml of N,N-dimethylformamide to which was added 3 mg of bis(triphenylphosphine) palladium (II) chloride and 13 mg of cuprous iodide. Next, 1.2 g of the 4-propylphenylacetylene obtained in step 2 was added and allowed to react at 50 to 60° C for 0.5 hour. After completion of the reaction, 35 ml of 9% hydrochloric acid was added to the reaction solution. After being extracted with chloroform, the crystals were washed with water three times to distill off the chloroform. The residue was purified by silica gel-chloroform column chromatography, followed by recrystallization with a mixed solvent of acetone and methanol to obtain 0.5 g of 4-propyl-3'-fluoro-4'-cyanotolan. The melting point of this compound (hereinafter referred to as the C-I point) was 67.2° C.

The following compounds were synthesized using the same method:

4-methyl-3'-fluoro-4'-cyanotolan;
4-ethyl-3'-fluoro-4'-cyanotolan;
4-butyl-3'-fluoro-4'-cyanotolan;
4-hexyl-3'-fluoro-4'-cyanotolan (C-I point of 63.8° C.);
4-heptyl-3'-fluoro-4'-cyanotolan;
4-octyl-3'-fluoro-4'-cyanotolan;
4-nonyl-3'-fluoro-4'-cyanotolan; and
4-desyl-3'-fluoro-4'-cyanotolan.

Example 2 (Synthesis of Compound 1-b)

Production of 4-propyl-3',5'-difluoro-4'-cyanotolan.

Step 1: 60 g of carbon tⒺtrabromide was dissolved in 180 ml of dichloromethane, and 93 g of triphenylphosphine was added at 0° C. or less. Next, 22 g of 4-propylbanzaldehyde was dissolved in 150 ml of dichloromethane, which then was added dropwise to the first dichloromethane solution over a period of one hour. The combined solutions were then agitated at room temperature for one hour. After completion of the reaction, the dichloromethane was distilled off, and 500 ml hexane was added to the residue. The resulting crystals were filtrated and further washed with hexane three times. The residue was subjected to vacuum distillation (120° to 130° C./4 mmHg) to obtain 27 g of 4-propyl-β,β-dibromostyrene.

Step 2: Under nitrogen flow, the 27 g of 4-propyl-β,β-dibromostyrene was dissolved in 44 ml of tetrahydrofuran and cooled to −78° C. Two hundred ml of a butyl lithium hexane solution (1.6 mol/l was added dropwise therein over a period of one hour. The solution was then agitated at room temperature for one and a half hours. After completion of the reaction, 200 ml of water was added. The crystals then were extracted with chloroform and washed three times with water. The remaining chloroform was distilled off, after which vacuum distillation (70° to 75° C./20 mmHg) was carried out to obtain 3.5 g of 4-propylphenylacetylene.

Step 3: 60 g of 2,6-difluoroaniline was dissolved in 180 ml of acetic acid. A solution containing 75 g of iodine chloride dissolved in 48 ml of acetic acid was added dropwise therein, and then agitated at 80° C. for 2 hours. The reaction solution was poured into water, and the resulting deposited crystals were filtrated and washed with water. The crystals were recrystallized with methanol, vacuum distilled (125° C./22 mmHg), and recrystallized again with methanol to obtain 57 g of 2,6-difluoro-4-iodoaniline.

Step 4: 12 g of sodium nitrite was dissolved in 91 ml of sulfuric acid and cooled to 10° C or less, and then 100 ml of acetic acid was added. At 20 to 25° C, 39 g of the 2,6-difluoro-4-iodoaniline from Step 3 was added to the solution, and then the solution was agitated for one hour. A second solution was made by dissolving 37 g of copper sulfate pentahydrate in 91 ml of water to which was added 62 g of ice, and this solution was added to the first. A third solution containing 39 of potassium cyanide dissolved in 92 ml of water, 221 g of sodium bicarbonate, and 91 ml of benzene was added to the first solution, and a diazonium salt sulfuric acid solution was added therein. After agitation at room temperature for 3 hours, a sodium hydroxide aqueous solution was added to dissolve the crystals. After being extracted with chloroform, the crystals were washed three times alternating with a 10% sodium hydroxide solution and water. After distillation of the chloroform, the residue was extracted with hexane, and the hexane was distilled off. This residue was recrystallized with methanol to obtain 6.7 g of 1,3-difluoro-2-cyano-5-iodobenzene.

Step 5: 5.6 g of this 1,3-difluoro-2-cyano-5-iodobenzene was dissolved in 35 ml of N,N-dimethylformamide, to which was added 7.3 mg of bis(triphenylphosphine) palladium (II) chloride and 34 m of cuprous iodide. Next, 3 g of the 4-propylphenylacetylene obtained in Step 2 was added and allowed to react at 50° to 60° C. for 0.5 hour. After completion of the reaction, 35 ml of 9% hydrochloric acid was added to the reaction solution. After being extracted with chloroform, the crystals were washed with water three times to distill off the chloroform. The residue was purified by silica gel-chloroform column chromatography, followed by recrystallization with a mixed solvent of acetone and methanol to obtain 1.6 g of 4-propyl-3',5'-difluoro-4'-cyanotolan. The melting (C-I) point of this compound was 83.3° C.

The following compounds were synthesized using the same method:

4-methyl-3',5'-difluoro-4'-cyanotolan;
4-ethyl-3',5'-difluoro-4'-cyanotolan;
4-butyl-3',5'-difluoro-4'-cyanotolan (C-I point of 69.5° C.);
4-pentyl-3',5'-difluoro-4'-cyanotolan;
4-hexyl-3',5'-difluoro-4'-cyanotolan (C-I point of 50.2° C.);
4-heptyl-3',5'-difluoro-4'-cyanotolan;
4-octyl-3',5'-difluoro-4'-cyanotolan;
4-nonyl-3',5'-difluoro-4'-cyanotolan; and
4-desyl-3',5'-difluoro-4'-cyanotolan.

Example 3 (Synthesis of Compound I-c)

Production of 4-(4'-butylphenyl)-3'-fluoro-4'-cyanotolan.

Step 1: 60 g of carbon tetrabromide was dissolved in 185 ml of dichloromethane, and 100 g of triphenylphosphine was added at 0° C. or less. Next, 22 g of 4'-butyl-4-biphenylaldehyde was dissolved in 93 ml of dichloromethane, which then was added dropwise to the first dichloromethane solution over a period of one hour. The combined solutions were then agitated at room temperature for one hour. After completion of the reaction, the dichloromethane was distilled off, and 500 ml hexane was added to the residue. The resulting crystals were filtrated and further washed with hexane three times. The residue was recrystallized with hexane to obtain 9.6 g of 4-(4'-butylphenyl)-$\beta,\beta$-dibromostyrene.

Step 2: Under nitrogen flow, the 9.6 g of 4-(4'-butylphenyl)-$\beta,\beta$-dibromostyrene was dissolved in 50 ml of tetrahydrofuran and cooled to −78° C. One hundred ml of a butyl lithium hexane solution (1.6 mol/l) was added dropwise therein over a period of one hour. The solution was then agitated at room temperature for one and a half hours. After completion of the reaction, 500 ml of water was added, the crystals were extracted with chloroform, and then washed three times with water. The remaining chloroform was distilled off, after which the solvent was completely removed to obtain 5 g of 4'-butyl-4-biphenylacetylene.

Step 3; Omitted.

Step 4: 27 g of sodium nitrite was dissolved in 205 ml of sulfuric acid and cooled to 10° C. or less, and then 238 ml of acetic acid was added. At 20° to 25° C., 65 g of 2-fluoro-4-iodoaniline was added to the solution, and then the solution was agitated for one hour. A second solution was made by dissolving 82.5 g of copper sulfate pentahydrate in 20.5 ml of water, to which was added 140 g of ice, and this solution was added to the first. A third solution containing 88 g of potassium cyanide dissolved in 207 ml of water, 500 g of sodium bicarbonate, and 206 ml of benzene was added to the first solution, and a diazonium salt sulfuric acid solution was added therein. After agitation at room temperature for 3 hours, a sodium hydroxide aqueous solution was added to dissolve the crystals. After being extracted with chloroform, the crystals were washed three times alternating with a 10% sodium hydroxide solution and water. After distillation of the chloroform, the residue was extracted with hexane, and the hexane was distilled off. This residue was subjected to vacuum distillation (95° to 110° C./15 mmHg), and further recrystallized to obtain 20 g of 1-cyano-2-fluoro-4-iodobenzene.

Step 5: 2.1 g of this 1-cyano-2-fluoro-4-iodobenzene was dissolved in 15 ml of N,N-dimethylformamide, to which was added 3 mg of bis(triphenylphosphine) palladium (II) chloride and 14 mg of cuprous iodide. Next, 2 g of the 4'-butyl-4-biphenylacetylene obtained in Step 2 was added and allowed to react at 50 to 60° C for 0.5 hour. After completion of the reaction, 35 ml of 9% hydrochloric acid was added to the reaction solution. After being extracted with chloroform, the crystals were washed with water three times to distill off the chloroform. The residue was purified by silica gel-chloroform column chromatography, followed by recrystallization with a mixed solvent of acetone and methanol to obtain 0.4 g of 4-(4''-butylphenyl)-3'-fluoro-4'-cyanotolan. The C-N point of this compound was 99.4° C., and the N-I point was 214.5° C.

The following compounds were synthesized using the same method:

4-(4''-methylphenyl)-3'-fluoro-4'-cyanotolan;
4-(4''-ethylphenyl)-3'-fluoro-4'-cyanotolan; 4-(4''-propylphenyl)-3'-fluoro-4'-cyanotolan (C-N point of 129.4° C., N-I point of 232.8° C.);
4-(4''-pentylphenyl)-3'-fluoro-4'-cyanotolan;
4-(4''-hexyphenyl)-3'-fluoro-4'-cyanotolan (C-N point of 64.2° C., N-I point of 198.4° C.);

4-(4″-heptylphenyl)-3′-fluoro-4′-cyanotolan (C-N point of 72.5° C., N-I point of 193.3° C.);
4-(4″-octylphenyl)-3′-fluoro-4′-cyanotolan;
4-(4″-nonylphenyl)-3′-fluoro-4′-cyanotolan; and 4-(4″-desylphenyl)-3′-fluoro-4′-cyanotolan.

Example 4 (Synthesis of Compound 1-d)

Production of 4-(4″-butylphenyl)-3′,5′-difluoro-4′-cyanotolan.

Step 1: 60 g of carbon tetrabromide was dissolved in 185 ml of dichloromethane, and 100 g of triphenylphosphine was added at 0° C. or less. Next, 22 g of 4′-butyl-4-biphenylaldehyde was dissolved in 93 ml of dichloromethane, which then was added dropwise to the first dichloromethane solution over a period of one hour. The combined solutions were then agitated at room temperature for one hour. After completion of the reaction, the dichloromethane was distilled off, and 500 ml hexane was added to the residue. The resulting crystals were filtrated and further washed with hexane three times. The residue was recrystallized with hexane to obtain 9.6 g of 4-(4′-butylphenyl)-β,β-dibromostyrene.

Step 2: Under nitrogen flow, the 9.6 g of 4-(4′-butylphenyl)-β,β-dibromostyrene was dissolved in 50 ml of tetrahydrofuran and cooled to −78° C. One hundred ml of a butyl lithium hexane solution (1.6 mol/1) was added dropwise therein over a period of one hour. The solution was then agitated at room temperature for one and a half hours. After completion of the reaction, 500 ml of water was added, the crystals were extracted with chloroform, and then washed three times with water. The remaining chloroform was distilled off, after which the solvent was completely removed to obtain 5 g of 4′-butyl-4-biphenylacetylene.

Step 3. Using the same method as Example 2, 2,6-difluoro-4-iodoaniline was obtained.

Step 4: Using the same method as Example 2, 1,3-difluoro-2-cyano-5-iodobenzene was obtained.

Step 5. 3 g of this 1,3-difluoro-2-cyano-5-iodobenzene was dissolved in 19 ml of N,N-dimethylformamide to which was added 4 mg of bis(triphenylphospine) palladium (II) chloride and 18 mg of cuprous iodide. Next, 3 g of the 4′-butyl-4-biphenylacetylene obtained in Step 2 was added and allowed to react at 50° to 60° C. for 0.5 hour. After completion of the reaction, 35 ml of 9% hydrochloric acid was added to the reaction solution After being extracted with chloroform, the crystals were washed with water three times to distill off the chloroform. The residue was purified by silica gel-chloroform column chromatography, followed by recrystallization with a mixed solvent of acetone and methanol to obtain 0.4 g of 4-(4′-butylphenyl)-3′,5′-difluoro-4′-cyanotolan. The C-N point of this compound was 101.0° C., and the N-I point was The following compounds were synthesized by using the same method:

4-(4″-methylphenyl)-3′,5′-difluoro-4′-cyanotolan;
4-(4″-ethylphenyl)-3′,5′-difluoro-4′-cyanotolan; 4-(4″-propylphenyl)-3′,5′-difluoro-4′-cyanotolan (C-N point of 142.8° C., N-I point of 182.8° C.);
4-(4″-pentylphenyl)-3′,5′-difluoro-4′-cyanotolan;
4-(4″-hexylphenyl)-3′,5′-difluoro-4′-cyanotolan (C-N point of 52.0° C., N-I point of 152.5° C.);
4-(4″-heptylphenyl)-3′,5′-difluoro-4′-cyanotolan (C-N point of 60.9° C., N-I point of 149.2° C.);
4-(4″-octylphenyl)-3′,5′-difluoro-4′-cyanotolan; 4-(4″-nonylphenyl)-3′,5′-difluoro-4′-cyanotolan; and 4-(4″-desylphenyl)-3′,5′-difluoro-4′-cyanotolan.

Example 5 (Synthesis of Compound 1-e)

Production of 4-(trans-4″-ethylcyclohexyl)-3′-fluoro-4′-cyanotolan.

Step 1: 148 g of carbon tetrabromide was dissolved in ml of dichloromethane, and 93 g of triphenylphospine was added at 0° C. or less. Next, 48.6 g of 4-(trans-4′-ethylcyclohexyl)benzaldehyde was dissolved in 225 ml of dichloromethane, which then was added dropwise to the first dichloromethane solution over a period of one hour. The combined solutions were then agitated at room temperature for one hour. After completion of the reaction, the dichloromethane was distilled off, and 500 ml of hexane was added to the residue. The resulting crystals were filtrated and further washed with hexane three times. The residue was subjected to recrystallization with hexane to obtain 52 g of 4-(trans-4′-ethylcyclohexyl)-β,β-dibromostyrene.

Step 2: Under nitrogen flow, the 52 g of 4-(trans-4′-ethylcyclohexyl)-β,β-dibromostyrene was dissolved in 250 ml of tetrahydrofuran and cooled to −78° C. Three hundred ml of a butyl lithium hexane solution (1.6 mol/1) was added dropwise therein over a period of one hour. The solution was then agitated at room temperature for one and a half hours. After completion of the reaction, 500 ml of water was added, the crystals were extracted with chloroform and then washed three times with water. The remaining chloroform, was distilled off, after which vacuum distillation (110° to 120° C./30 mmHg) was carried out to obtain 20 g of 4-(trans-4′-ethylcyclohexyl)acetylene.

Step 3: Omitted.

Step 4: 27 g of sodium nitrite was dissolved in 205 ml of sulfuric acid and cooled to 10° C. or less, and then 238 ml of acetic acid was added. At 20° to 25° C., 65 g of 2-fluoro-4-iodoaniline was added to the solution, and then the solution was agitated for one hour. A second solution was made by dissolving 82.5 g of copper sulfate pentahydrate in 20.5 ml of water, to which was added 140 g of ice, and this solution was added to the first. A third solution containing 88 g of potassium cyanide dissolved in 207 ml of water, 500 g of sodium bicarbonate, and 206 ml of benzene was added to the first solution, and a diazonium salt sulfuric acid solution was added therein. After agitation at room temperature for 3 hours, a sodium hydroxide aqueous solution was added to dissolve the crystals. After being extracted with chloroform, the crystals were washed three times alternating with a 10% sodium hydroxide solution and water. After distillation of the chloroform, the residue was extracted with hexane, and the hexane was distilled off. This residue was subjected to vacuum distillation (95° to 110° C./15 mmHg), and further recrystallized to obtain 20 g of 1-cyano-2-fluoro-4-iodobenzene.

Step 5: 3.8 g of this 1-cyano-2-fluoro-4-iodobenzene was dissolved in 25 ml of N,N-dimethylformamide, to which was added 5.3 mg of bis(triphenylphosphine) palladium (II) chloride and 25 mg of cuprous iodide. Next, 3.2 g of the 4-(trans-4′-ethylcyclohexyl)acetylene obtained in Step 2 was added and allowed to react at 50° to 60° C. for 0.5 hour. After completion of the reaction, 3.5 ml of 9% hydrochloric acid was added to the reaction solution. After being extracted with chloroform, the crystals were washed with water three times to distill off the chloroform. The residue was purified by silica gel-chloroform column chromatography, followed by recrystallization with a mixed solvent of acetone and methanol to obtain 0.8 g of 4-(trans-4′-ethylcyclohexyl)-3″-fluoro-4‴-cyanotolan. The C-N point of this compound was 129.3° C., and the N-I point was 201.3° C.

The following compounds were synthesized using the same method:
  4-(trans-4″-methylcyclohexyl)-3′-fluoro-4′-cyanotolan;
  4-(trans-4″-propylcyclohexyl)-3′-fluoro-4′-cyanotolan (C-N point of 113.3° C., N-I point of 213.8° C.);
  4-(trans-4″-butylcyclohexyl)-3′-fluoro-4′-cyanotolan;
  4-(trans-4″-pentylcyclohexyl)-3′-fluoro-4′-cyanotolan;
  4-(trans-4″-hexylcyclohexyl)-3′-fluoro-4′-cyanotolan;
  4-(trans-4″-heptylcyclohexyl)-3′-fluoro-4′-cyanotolan;
  4-(trans-4″-octylcyclohexyl)-3′-fluoro-4′-cyanotolan;
  4-(trans-4″-nonylcyclohexyl)-3′-fluoro-4′-cyanotolan; and
  4-(trans-4″-desylcyclohexyl)-3′-fluoro-4′-cyanotolan.

Example 6 (Synthesis of Compound 1-f)

Production of 4-(trans-4′-propylcyclohexyl)-3′,5′-difluoro-4′-cyanotolan.

Step 1: 26.9 g of carbon tetrabromide was dissolved in 82 ml of dichloromethane, and 42.6 g of triphenylphosphine was added at 0° C. or less. Next, 10 g of 4-(trans-4′-propylcyclohexyl)benzaldehyde was dissolved in 41 ml of dichloromethane, which then was added dropwise to the first dichloromethane solution over a period of one hour. The combined solutions were then agitated at room temperature for one hour. After completion of the reaction, the dichloromethane was distilled off, and 500 ml of hexane was added to the residue. The resulting crystals were filtrated and washed with hexane three times. The residue was subjected to recrystallization with hexane to obtain 16 g of 4-(trans-4′-propylcyclohexyl)-β,β-dibromostyrene.

Step 2: Under nitrogen flow, the 16 g of 4-(trans-4′-propylcyclohexyl)-β,β-dibromostyrene was dissolved in 76 ml of tetrahydrofuran and cooled to −78° C. One hundred ml of a butyl lithium hexane solution (1.6 mol/l) was added dropwise therein over a period of one hour. The solution was then agitated at room temperature for one and a half hours. After completion of the reaction, 200 ml of water was added, the crystals were extracted with chloroform, and then washed three times with water. The remaining chloroform was distilled off, after which recrystallization was carried out with methanol to obtain 2.45 g of 4-(trans-4′-propylcyclohexyl)acetylene.

Step 3: Using the same method as Example 2, 2,6-difluoro-4-iodoaniline was obtained.

Step 4: Using the same method as Example 2, 1,3-difluoro-2-cyano-5-iodobenzene was obtained.

Step 5: 2.5 g of this 1,3-difluoro-2-cyano-5-iodobenzene was dissolved in 15 ml of N,N-dimethylformamide, to which was added 3.3 mg of bis(triphenylphosphine) palladium (II) chloride and 15 mg of cuprous iodide. Next, 2.45 g of the 4-(trans-4′-propylcyclohexyl)acetylene obtained in Step 2 was added and allowed to react at 50 to 60° C. for 0.5 hour. After completion of the reaction, 29 ml of 9% hydrochloric acid was added to the reaction solution. After being extracted with chloroform, the crystals were washed with water and were washed twice with 10% hydrochloric acid, 5% hydrogencarbonate aqueous solution, and water, in that order. The chloroform was distilled off, and the residue was purified by column chromatography. Vacuum distillation (150° to 160° C./3 mmHg) was performed, and the residue was further recrystallized with a mixed solvent of acetone and methanol to obtain 0.3 g of 4-(trans-″-propylcyclohexyl)-3′,5′-difluoro-4′-cyanotolan. The C-N point of this compound was 105.2° C., and the N-I point was 175.0° C. The following compounds were synthesized using the same method:
  4-(trans-4″-methylcyclohexyl)-3′,5′-difluoro-4′-cyanotolan;
  4-(trans-4″-ethylcyclohexyl)-3′,5′-difluoro-4′-cyanotolan (C-N point of 121.8° C., N-I point of 150.4° C.);
  4-(trans-4″-butylcyclohexyl)-3′,5′-difluoro-4′-cyanotolan (C-N point of 146.2° C., N-I point of 170.4° C.);
  4-(trans-4″-pentylcyclohexyl)-3′,5′-difluoro-4′-cyanotolan (C-N point of 99.5° C., N-I point of 172.4° C.);
  4-(trans-4″-hexylcyclohexyl)-3′,5′-difluoro-4-cyanotolan;
  4-(trans-4″-heptylcyclohexyl)-3′,5′-difluoro-4-cyanotolan;
  4-(trans-4″-octylcyclohexyl)-3′,5′-difluoro-4-cyanotolan;
  4-(trans-4″-nonylcyclohexyl)-3′,5′-difluoro-4-cyanotolan;
  4-(trans-4″-desylcyclohexyl)-3′,5′-difluoro-4-cyanotolan; and
  4-(trans-4″-propylcyclohexyl)-3′,5′-difluoro-4-cyanotolan.

Examples 7 to 12 (using Examples 1–6)

Six liquid crystal compositions (Examples 7–12) containing compounds made in accordance with the invention were compared with two liquid crystal compositions (comparative tests A and B) not containing the tolan compounds made in accordance with the invention. A commercially available mixed liquid crystal material ZLI-1565 (a product of Merck Co., Ltd., N-I point of 89.3° C.) was used as a base liquid crystal in all eight compositions. 4-butylbenzoic acid 4′-cyanophenyl ester was used in comparative test A to decrease $V_{th}$, and 4-pentyl-4″-cyanoterphenyl was used in comparative test B to increase the N-I point and $\Delta n$. The components in each compound are shown in Table 1:

TABLE 1

| | ZLI-ZLI- | A | B | 1-a | 1-b | 1-c | 1-d | 1-e | 1-f |
|---|---|---|---|---|---|---|---|---|---|
| Comparative Test A | 90 pbw | 10 pbw | | | | | | | |
| Comparative Test B | 90 pbw | | 10 pbw | | | | | | |
| Example 7 | 90 pbw | | | 10 pbw | | | | | |
| Example 8 | 90 pbw | | | | 10 pbw | | | | |
| Example 9 | 90 pbw | | | | | 10 pbw | | | |
| Example 10 | 90 pbw | | | | | | 10 pbw | | |
| Example 11 | 90 pbw | | | | | | | 10 pbw | |

TABLE 1-continued

| | ZLI-ZLI- | A | B | 1-a | 1-b | 1-c | 1-d | 1-e | 1-f |
|---|---|---|---|---|---|---|---|---|---|
| Example 12 | 90 pbw | | | | | | | | 10 pbw |

A: 4-butylbenzoic acid 4'-cyanophenyl ester
B: 4-pentyl-4''-cyanoterphenyl
1-a: 4-propyl-3'-fluoro-4'-cyanotolan
a-b: 4-propyl-3',5'-difluoro-4'-cyanotolan
1-c: 4-(4''-butylphenyl)-3'-fluoro-4'-cyanotolan
1-d: 4-(4''-butylphenyl)-3',5'-difluoro-4'-cyanotolan
1-e: 4-(trans-4''-ethylcyclohexyl)-3'-fluoro-4'-cyanotolan
1-f: 4-(trans-4''-ethylcyclohexyl)-3',5'-difluoro-4'-cyanotolan
pbw: parts by weight Liquid crystal cells 10 as shown in FIG. 1 were assembled to compare the performance of the liquid crystal compositions. Electrodes 13 and 14 of transparent conductive films such as ITO films were formed on glass substrates 11 and 12. Orientation materials of polyimide or similar material was applied over electrodes 13 and 14 to form orientation-regulating layers 19 and 21. Glass substrates 11 and 12 were sealed with sealing member 16 to provide liquid crystal cell 10. The liquid crystal compositions listed in Table 1 were each poured into a separate liquid crystal cell 10.

Each cell 10 had a thickness of 8 μm and was of the TN type. The liquid crystal cells thus prepared were subjected to alternating current static driving at 20° C. to measure the voltage-brightness characteristics. The comparative results are shown in Table 2.

TABLE 2

| | N-I Point | Δn | $V_{10}$ | α | β |
|---|---|---|---|---|---|
| Comparative Test A | 83.6° C. | 0.133 | 2.032 | 1.275 | 1.405 |
| Comparative Test B | 100.8° C. | 0.149 | 2.415 | 1.292 | 1.425 |
| Example 7 | 80.8° C. | 0.146 | 1.962 | 1.286 | 1.380 |
| Example 8 | 76.5° C. | 0.140 | 1.710 | 1.285 | 1.379 |
| Example 9 | 97.4° C. | 0.158 | 2.200 | 1.289 | 1.398 |
| Example 10 | 93.0° C. | 0.154 | 1.927 | 1.282 | 1.388 |
| Example 11 | 94.8° C. | 0.147 | 2.121 | 1.291 | 1.403 |
| Example 12 | 91.3° C. | 0.144 | 1.895 | 1.302 | 1.397 |

$V_{10}$ is the voltage value when the transmittance is 10%, which is the measured value from a TN cell with the measuring direction $\theta = 90°$. In addition, α and β are factors representing a visual angle characteristic and a threshold characteristic, respectively, which have been defined as follows:

$\alpha = \theta 90° V_{50} / \theta 50° V_{50}$
$\beta = \theta 90° V_{10} / \theta 90° V_{90}$ Although a TN-type liquid crystal cell was used in the examples, the same effects are realized even when a super twisted nematic type (STN) liquid crystal cell is used.

As described above, the tolan compounds prepared in accordance with the invention may be mixed into a general liquid crystal composition. Thus, without deteriorating electro-optical characteristics (α value and β value), the threshold voltage is greatly decreased and Δn is increased. Moreover, as demonstrated with compounds 1-c, 1-d, 1-e and 1-f, the temperature range for practical use is wide. Compounds made in accordance with the invention are, therefore, useful as basic constituent components of liquid crystal compositions in the super twisted nematic type display devices which are dominant in current liquid crystal display devices.

It will thus be seen that the objects set forth above, among those made apparent from the preceding description, are efficiently attained and, since certain changes may be made in carrying out the above process, in the described product, and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

WHAT IS CLAIMED IS:

1. A tolan derivative represented by the general formula:

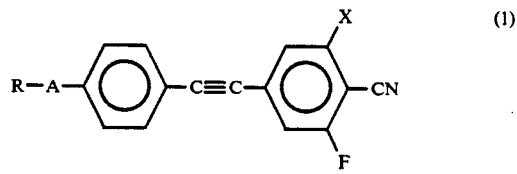

(1)

wherein R is a straight chain alkyl group having from 1 to 10 carbon atoms, A is either

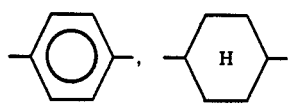

or a single bond, and X is hydrogen or fluorine.

2. The tolan derivative of claim 1 represented by the general formula:

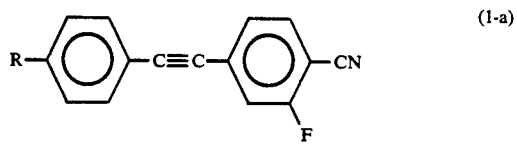

(1-a)

wherein R is a straight chain alkyl group having from 1 to 10 carbon atoms.

3. The tolan derivative of claim 1 represented by the general formula:

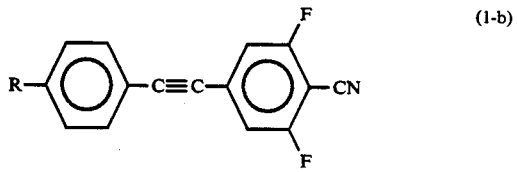

(1-b)

wherein R is a straight chain alkyl group having from 1 to 10 carbon atoms.

4. The tolan derivative of claim 1 represented by the general formula:

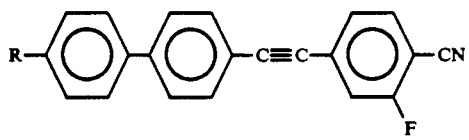 (1-c)

wherein R is a straight chain alkyl group having from 1 to 10 carbon atoms.

5. The tolan derivative of claim 1 represented by the general formula:

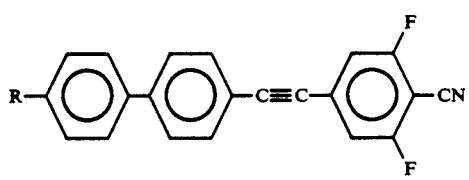 (1-d)

wherein R is a straight chain alkyl group having from 1 to 10 carbon atoms.

6. The tolan derivative of claim 1 represented by the general formula:

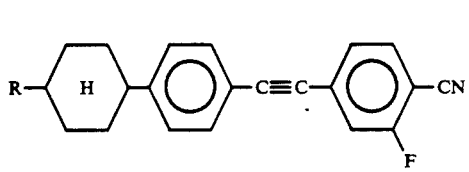 (1-e)

wherein R is a straight chain alkyl group having from 1 to 10 carbon atoms and the cyclohexane ring has the trans configuration.

7. The tolan derivative of claim 1 represented by the general formula:

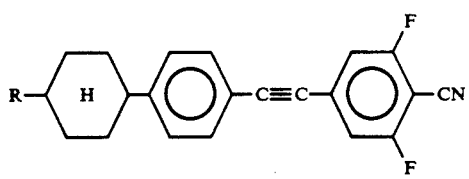 (1-f)

wherein R is a straight chain alkyl group having from 1 to 10 carbon atoms and the cyclohexane ring has the trans configuration.

8. A tolan derivative according to claim 1, wherein the tolan derivative is 4-propyl-3'-fluoro-4'-cyanotolan.

9. A tolan derivative according to claim 1, wherein the tolan derivative is 4-propyl-3',5'-difluoro-4'-cyanotolan.

10. A tolan derivative according to claim 1, wherein the tolan derivative is 4-(4''-butylphenyl)-3'-fluoro-4'-cyanotolan.

11. A tolan derivative according to claim 1, wherein the tolan derivative is 4-(4''-butylphenyl)-3',5'-difluoro-4'-cyanotolan.

12. A tolan derivative according to claim 1, wherein the tolan derivative is 4-(trans-4''-ethylcyclohexyl)-3'-fluoro-4'-cyanotolan.

13. A tolan derivative according to claim 1, wherein the tolan derivative is 4-(trans-4''-ethylcyclohexyl)-3',5'-difluoro-4'-cyanotolan.

14. A liquid crystal composition, including a tolan derivative represented by the general formula:

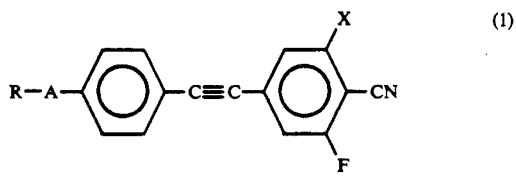 (1)

wherein R is a straight chain alkyl group having from 1 to 10 carbon atoms, A is either

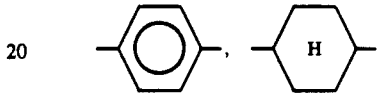

or a single bond, and X is hydrogen or fluorine.

15. The liquid crystal composition of claim 14, wherein X is hydrogen.

16. The liquid crystal composition of claim 14, wherein is X is fluorine.

17. The liquid crystal composition of claim 14, wherein A is

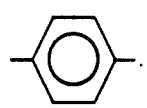.

18. The liquid crystal composition of claim 14, wherein A is

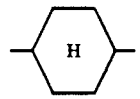

in the trans configuration.

19. The liquid crystal composition of claim 14, wherein A is a single bond.

20. The liquid crystal composition of claim 14, wherein the tolan derivative is included in an amount between about 2 to 20 weight percent based on a total weight of the composition.

21. A liquid crystal display cell including a pair of spaced apart opposed electrode substrates, a liquid crystal material in the space between the substrates, and spacer means for separating the substrates, the liquid crystal material including at least one of a compound represented by the general formula:

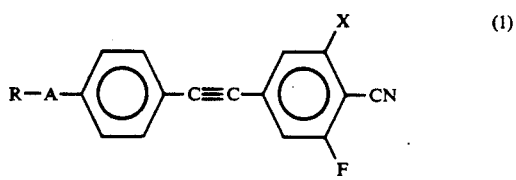 (1)

wherein R is a straight chain alkyl group having from 1 to 10 carbon atoms, A is either

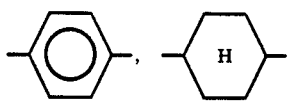

or a single bond, and X is hydrogen or fluorine.

22. The liquid crystal display cell of claim 21, wherein X is hydrogen.

23. The liquid crystal display cell of claim 21, wherein is X is fluorine.

24. The liquid crystal display cell of claim 21, wherein A is

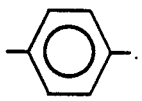

25. The liquid crystal display cell of claim 21, wherein A is

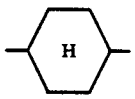

in the trans configuration.

26. The liquid crystal display cell of claim 21, wherein A is a single bond.

* * * * *